United States Patent
Schmid et al.

(10) Patent No.: US 9,265,961 B2
(45) Date of Patent: Feb. 23, 2016

(54) SUPPORT DEVICE FOR SUPPORTING A TRANSMISSION COIL ON THE BODY OF A PATIENT

(71) Applicant: Dualis MedTech GmbH, Seefeld (DE)

(72) Inventors: Thomas Schmid, Schondorf (DE); Stefan Auracher, Herrsching (DE); Stefan Schwarzbach, Gilching (DE)

(73) Assignee: DUALIS MEDTECH GMBH, Seefeld (DE)

( * ) Notice: Subject to any disclaimer, the term of this patent is extended or adjusted under 35 U.S.C. 154(b) by 31 days.

(21) Appl. No.: 14/373,808

(22) PCT Filed: Jan. 22, 2013

(86) PCT No.: PCT/EP2013/051131
§ 371 (c)(1),
(2) Date: Jul. 22, 2014

(87) PCT Pub. No.: WO2013/110602
PCT Pub. Date: Aug. 1, 2013

(65) Prior Publication Data
US 2014/0358211 A1    Dec. 4, 2014

(30) Foreign Application Priority Data

Jan. 25, 2012  (DE) .......................... 10 2012 201073

(51) Int. Cl.
| | |
|---|---|
| *A61N 1/378* | (2006.01) |
| *A61N 1/372* | (2006.01) |
| *A61N 1/375* | (2006.01) |
| *A61N 1/08* | (2006.01) |

(52) U.S. Cl.
CPC .......... *A61N 1/375* (2013.01); *A61N 1/08* (2013.01); *A61N 1/3787* (2013.01); *A61N 1/37229* (2013.01)

(58) Field of Classification Search
CPC ........... A61N 1/37211; A61N 1/37223; A61N 1/3787; A61N 1/40; A41D 13/1281; A61B 5/68; A61B 5/6801; A61B 5/6802; A61B 5/6803; A61B 5/6804; A61B 5/6805
USPC ........... 607/33, 60, 61, 65, 149; 600/386–390
See application file for complete search history.

(56) References Cited

U.S. PATENT DOCUMENTS

| | | | |
|---|---|---|---|
| 2005/0054941 A1* | 3/2005 | Ting ..................... | A61B 5/0408 600/529 |
| 2005/0107847 A1* | 5/2005 | Gruber ................. | A61N 1/3787 607/61 |
| 2005/0143786 A1* | 6/2005 | Boveja ............... | A61N 1/36025 607/45 |
| 2005/0192644 A1 | 9/2005 | Boveja et al. | |

(Continued)

OTHER PUBLICATIONS

International Search Report dated Mar. 14, 2013 for PCT application No. PCT/EP2013/051131.

*Primary Examiner* — Allen Porter, Jr.
(74) *Attorney, Agent, or Firm* — Ohland, Greeley, Ruggiero & Perle, L.L.P.

(57) ABSTRACT

A support device for supporting a transmission coil on the body of a patient, with a receiving or securing device or a receiving space for receiving or securing the transmission coil in and/or on the support device, and further comprising a detection device for detecting a process of application, a state of application, a process of removal and/or a state of removal of the support device relative to the body of the patient. Further pertaining to a method for operating such a device.

8 Claims, 1 Drawing Sheet

(56) References Cited

U.S. PATENT DOCUMENTS

| | | | |
|---|---|---|---|
| 2005/0228462 A1* | 10/2005 | Brighton | A61N 2/02 607/51 |
| 2006/0122544 A1* | 6/2006 | Ciluffo | A41D 13/0015 601/15 |
| 2007/0123948 A1 | 5/2007 | Dal Molin | |
| 2008/0103407 A1* | 5/2008 | Bolea | A61N 1/0556 600/529 |
| 2009/0024062 A1* | 1/2009 | Einarsson | A41D 13/1281 600/595 |
| 2009/0204013 A1* | 8/2009 | Muhlsteff | A41B 9/001 600/506 |
| 2010/0114143 A1 | 5/2010 | Albrecht | |

* cited by examiner

SUPPORT DEVICE FOR SUPPORTING A TRANSMISSION COIL ON THE BODY OF A PATIENT

BACKGROUND

1. Field of the Disclosure

The disclosure relates to a support device for supporting a transmission coil on the body of a patient.

2. Discussion of the Background Art

It is known to supply implants, such as artificial hearts or cardiac support systems, with energy in a wireless manner by means of inductive coupling using an implanted receiving coil and an extracorporeal transmission coil. For this purpose, the transmission coil is connected to a voltage source so that electric alternating voltage is supplied thereto, which generates an alternating magnetic field. The receiving coil arranged in the area of this magnetic field generates an electric voltage by induction, which voltage is supplied to the implant.

In order to achieve an energy transmission with a high degree of efficiency, it is important to arrange the transmission coil exactly over the implanted receiving coil. An offset between the transmission coil and the receiving coil, both in the radial and in the axial direction, compromises the degree of efficiency of the energy transmission. Further, the support device, by which the transmission coil is supported on the body of a patient, should possibly be worn in a comfortable manner on the body of a patient and hinder the same as little as possible during his daily activities.

It is known to fasten the transmission coil on the body of a patient by means of a fastening or support device, so that the former can be coupled inductively with the implanted receiving coil. Such a supporting device may be designed as a belt, for example. There is a problem that energy transmission can no longer be ensured, if such a support device slips and the transmission coil is therefore no longer situated exactly over the receiving coil. Further, external effects may cause an inadvertent shedding of such a support device so that also in this case no energy can be transmitted anymore. Such scenarios can lead to dangerous, sometimes perilous situations.

It is an object of the present disclosure to provide a support device for supporting a transmission coil on the body of a patient, which allows achieving a more reliable energy transmission to an implanted receiving coil.

SUMMARY

The support device for supporting a transmission coil on the body of a patient comprises a receiving or securing device or a receiving space for holding or fastening the transmission coil in and/or at the support device. For example, the receiving device or the receiving space may be a pocket which is formed on the support device and into which the transmission coil is inserted such that it can be held at a defined position on the body of a patient. It is also possible to fasten the transmission coil on the support device in a different manner. All that matters in this regard is that the transmission coil is fastened such on the support device that it is arranged in a defined abutment position relative to the body of a patient.

In a particular embodiment of the disclosure the coil may be realized in the form of electrically conductive elements, such as strands, which are woven into the support device and are wound in a coil-like manner, whereby a particularly high wearing comfort can be achieved.

The support device of the present disclosure may take different forms and can be designed as a waistcoat, a belt or a bustier, for example. The support device of the present disclosure comprises a detection device for detecting a put-on process, a put-on state, a put-off process and/or a put-off state of the support device relative to the body of a patient. The detection device is thus adapted to detect at least one of the actions or states mentioned, i.e., whether the support device is being put on the body of a patient, whether the support device is put on the body of a patient, whether the support device is being put off the body of a patient, or whether the support device has already been put off at the current time and is thus no longer on the body of a patient.

Owing to the above mentioned detecting device, the support device of the present disclosure thus has the important information whether the support device is placed correctly on the body of a patient and whether a proper energy transmission is possible. Should this not be the case, appropriate measures can be taken that will be described hereinafter. Thus, the disclosure provides an intelligent support device which makes it possible to avoid dangerous and possible life-threatening situations, since it considers information about the support state that were not available before.

BRIEF DESCRIPTION OF THE DRAWINGS

The following is a description of preferred embodiments of the disclosure with reference to Figures.

In the Figures.

DETAILED DESCRIPTION OF THE PREFERRED EMBODIMENT

Figure 1:
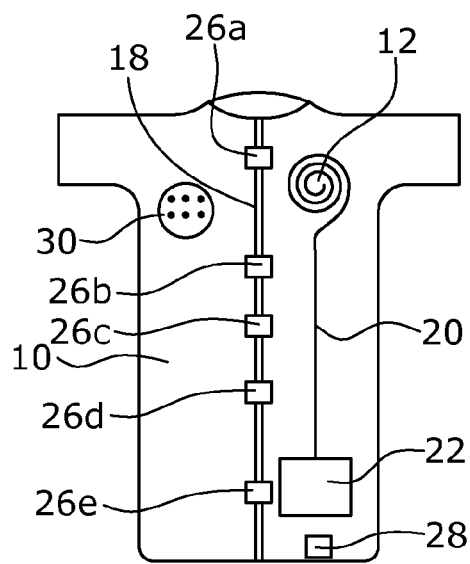
FIG. 1 is a front view of an embodiment of the support device of the present disclosure.

In a preferred embodiment, the support device comprises a closure device for the detachable fastening of the support device on the body of a patient. For example, this can be a zipper, one or more Velcro or snap locks or similar closure devices. The detecting device can be formed in or at the closure device such that the detection device can detect an opening of the closure device and, in the case of a plurality of closure devices, it can detect in particular the temporal course of the process of opening the plurality of closure devices. Thereby, the support device of the present disclosure has the information on whether the closure device has been opened, as well as on the type and the temporal course of the opening process, if applicable. It is possible to obtain information from the temporal course of the opening process on whether the closure device has been opened intentionally or unintentionally. Further details on this aspect will be described in the further course of the description of the present application in the context of the method of the present disclosure.

It is possible, for example, to provide one detection device on one closure device, respectively, so that it can be detected at what moment which closure device has been opened. Further, a plurality of detection devices can be arranged along a single closure device, such as a zipper, for example, so that it can be detected in which manner and at which speed the zipper has been opened. If, for example, the zipper is not opened in the appropriate direction, for example from the top to the bottom, it can be assumed that it was opened unintentionally by the action of an external force and that, therefore, the subsequent shedding of the support device was not intended. In this case, a corresponding alarm can be output or further counter-measures can be taken. For example, it is further possible that a closure device, e.g. a zipper, is opened unintentionally by movements of a patient, such as during sleep. Typically, this comes about over a relatively long period of time. Thus, if the detection devices detect an opening of the closure device or the closure devices over a period of time longer than a defined threshold value, an unintentional opening of the closure device can be assumed.

Further, the extent to which a closure device has been closed by a patient can be interesting information. In order to obtain this information, a plurality of detection devices can be arranged along the closure device or at a plurality of closure devices, for example, by which it is detected whether the closure device is closed at that point. For example, it can be detected thereby whether a zipper has been closed completely by a patient. If this is not the case, it is assumed that the transmission coil is possibly not positioned correctly, so that an alarm is output.

The support device of the present disclosure can further comprise an input device for inputting information into the support device about an intentional shedding of the support device by the user. Thus, via this input means, the user can supply the support device with the information that he has put off or will put off the support device intentionally. The input device may, for example, be a voice input device, such as a microphone, or at least a key. This can also be a software key on a touch display that is not configured as a hardware key. In this embodiment, the support device further comprises an alarm device for outputting an alarm signal when the support device is put off or shifted unintentionally. As an alternative or in addition, the support device can be connected to such an alarm device via a data link so that it is possible to output the alarm in another location. For example, the alarm could be routed to a medical facility so that a doctor, a healthcare worker or other assistance personnel can initiate corresponding emergency measures in the event of an unintentional shedding of the support device. Such a transmission of the alarm signal can also be effected over greater distances, for example, via a communication network, in particular a wireless network. An alarm signal or other information about the support state or the health condition of a patient can also be transmitted to another electronic device, e.g. a smart phone or a watch worn by the patient. The alarm device will not emit an alarm signal provided that the user has inputted information about an intentional shedding of the support device into the input device. The alarm will be emitted only, if the support device assumes that it has been put off unintentionally. In this way, false alarms can be avoided, which would otherwise cause unnecessary trouble to the patient as well as to the assistance personnel.

In this manner, in specific situations, such as before taking a shower, the user has the possibility to give the support device the information that the support device will now be put off intentionally so that no alarm is output. During the time that the support device is put off, the implant is supplied with energy by an accumulator that is also implanted. After having taken a shower, the user can put on the support device again so that the transmission and receiving coil are again coupled with each other and the inductive energy transmission can be performed again. At this time, the patient can supply the support device with further information indicating that the intentional process of putting on the support device is now completed so that, when the support device is put off again, it can be assumed that this has happened unintentionally.

Further, the support device can comprise a sensor for detecting movements of a patient or of the position of a patient. For example, this may be a GPS sensor. As an alternative, the position can be determined using the GSM network. Further, a position sensor can be provided to detect the orientation of a patient. Using the sensors mentioned it is possible to detect in particular the temporal course of the movements and the orientation of a patient. From this, it is possible to obtain important information about the treatment progress. Moreover, this information can be useful to the manufacturer of the support device, since he can thus adapt the support device to the wearing behavior of the patients. For example, it can be detected how often a patient puts off the support device. As an alternative or in addition, the charging behavior can be detected. This means that it is detected at what intervals and for how long the implanted accumulator is charged by means of the transmission coil in the support device. This makes it possible to obtain important information with regard to the dimensioning of the accumulator.

Further, the support device of the present disclosure can comprise an offset detection device for detecting an axial or radial offset between the transmission coil, arranged in or on the support device, and a receiving coil implanted in the body of a patient. Such an offset detection device can be formed, for example, by magnetic field sensors in the area of the implanted receiving coil, which detect the strength and/or the direction of the magnetic field generated by the transmission coil. As an alternative or in addition, electric parameters, such as the voltage induced into the receiving coil, the current or the phase position can be measured in the receiving coil. From these parameters, an offset between the transmission coil and the receiving coil can also be derived. In the embodiment mentioned, the support device further includes an alarm device, wherein in case of an offset that exceeds the defined threshold value an alarm signal is emitted unless information has been inputted by the patient at the input device indicating the intentional shedding of the transport device.

In a particular embodiment, the offset detection device described can also be combined with the above described detection device for detecting the closing state of the closure device. If, for example, an interrogation of a detection device yields that the closure device or the closure devices are closed completely and the offset detection device simultaneously indicates an offset between the transmission coil and the receiving coil, it can be assumed that the support device has been removed unintentionally from a patient's body or has been shifted unintentionally relative to the body of a patient. In this case, an alarm signal can be emitted.

In further embodiments, the support device can comprise different sensors allowing the acquisition of further information about the wearing condition. For example, the support device can have an acceleration sensor arranged in a closure device and/or in a support device itself. In case of an acceleration sensor provided in the closure device, such as a zipper, the temporal course of the opening process of the closure device can be detected. From this, information can be derived about whether the closure device has been opened intentionally or unintentionally. An unintentional opening can be assumed, for example, if the closure device has been opened over a very long period of time, for instance during sleep.

In addition or as an alternative, the support device can comprise a sleep detection sensor for detecting a sleeping state of a patient. The sleeping state of a patient can be detected, for example, by means of a position sensor, a movement sensor and/or a breathing frequency sensor. Based on the information about the sleeping state, the alarm can be emitted in various manners, for example. For instance, at night, while the patient sleeps, the alarm output can be delayed, if an unintentional shedding or shifting of the support device has been detected. In this situation, the implant can first be powered by the implanted accumulator. Possibly, during this time, the transmission coil is re-positioned correctly over the receiving coil by a movement the patient makes, so that an alarm can be avoided and the patient's sleep is not disturbed.

In addition or as an alternative, the support device can comprise a proximity sensor. Preferably, the proximity sensor is arranged on the inner side of the support device, i.e. facing the body of a patient. Thus, the proximity sensor makes it possible to detect whether the support device is put on the body of a patient.

In addition or as an alternative, the support device can include a breathing detection sensor for detecting the breathing of a patient. This may be an expansion sensor, for example. If it is detected that the patient does not breathe or does not breathe in a certain way, a corresponding alarm can be emitted.

Further, the support device of the present disclosure can comprise a strain sensor or a pressure sensor by which it can be detected, whether support device sits sufficiently tight on the body of a patient, wherein an alarm can also be emitted if it fits to loosely. Such a sensor can be arranged in the closure device or at another location on the support device.

The support device can further comprise a sensor for measuring the resistance of a contact surface, in particular of the human skin. Measuring the skin resistance makes it possible to detect, whether the support device is currently worn on a patient's body.

The sensors mentioned can thus be used individually or in combination with each other to acquire information about the wearing condition, especially about a change in the wearing condition, of the support device relative to the body of a patient and to evaluate the same thereafter. In particular, it is preferred to combine the information from a plurality of sensors with each other and to evaluate this merged sensor information so that it is possible to interpret a plurality of individual actions or processes. This allows for a more exact decision about whether the support device was put off intentionally or not.

The support device can comprise further sensors with which other parameters are measured that can provide information about the health condition of a patient, for example. The support device can, for instance, comprise a humidity sensor for measuring the humidity of a contact surface, especially the skin of a patient. If the measured humidity exceeds a defined threshold value, an alarm can be emitted, for example.

Should an offset be detected between the transmission and receiving coils, the transmission power of the transmission coil can be adapted automatically. For instance, the transmission coil may be supplied with a higher voltage for the generation of a stronger magnetic field. As an alternative or in addition, the magnetic field strength can be adapted by means of a ferromagnetic element at the transmission or the receiving coil, which element is movable or variable in volume or size.

If an unintentional shedding of the support device is detected in one of the above method steps, it is also possible to first increase the transmission power. It is checked, whether a sufficient energy transmission can still be achieved with this increase in transmission power. This can be the case, for example, when a patient has put off the support device, but the same is still close to the body of a patient and the transmission coil is positioned relative to the receiving coil such that energy can still be transmitted. If this is no longer possible, the transmission coil is no longer supplied with voltage, and an alarm is emitted.

The disclosure further relates to a method for detecting the wearing state of a support device for supporting a transmission coil on the body of a patient, in particular of a support device of the type described above. The present method comprises the following steps:

First, an intentional or unintentional action, a chronological sequence of intentional and/or unintentional actions and/or of a plurality of simultaneous intentional and/or unintentional actions of a patient are detected, which actions can result in or cause a shedding of the support device or a shifting of the support device relative to the body of a patient. An action of a patient also includes an action that a patient has not performed himself, but which can have an influence on the wearing state of the support device and can in particular cause the support device to move away from the body of a patient or to be shifted relative to the body. The detected action or actions of a patient are evaluated. Subsequently, it is decided, based on this evaluation, whether a patient has put off and/or shifted the support device intentionally or unintentionally. An alarm signal is emitted only if the support device has been put off and/or shifted unintentionally.

It is preferred that the evaluation of the action or actions of a patient comprises the following steps:

It is interrogated whether a patient has inputted information about an intentional shedding of the support device into an input device on the support device. In this case, no alarm signal is emitted.

Further, the evaluation of the action or actions of a patient can comprise the following steps:

A combination of a plurality of simultaneous or successive actions of a patient is interpreted, which actions have been detected in particular by a plurality of sensors. From this, information is derived about whether the shedding or shifting of the support device was intentional or unintentional.

In a particularly preferred embodiment of the present method, the temporal course of the opening process of at least one closure device by which the support device can be releasably secured on the body of a patient. An intentional shedding of the support device is assumed, if the detected progress of the detected opening process corresponds to a predefined reference progress within defined threshold values. This predefined reference progress has been determined beforehand in test measurements and has been stored digitally in the support device. If the detected progress of the detected opening process does not correspond to the predefined reference progress within defined threshold values, an unintentional shedding or shifting of the support device is assumed, so that a corresponding alarm can be emitted.

Due to the method of the present disclosure it is thus possible to detect and interpret human actions based on various information from sensors, so that more accurate information about the wearing state, and in particular about a change in the wearing state, can be obtained.

In a particularly preferred embodiment, the closure device, by which the support device is secured on the body of a patient, can be configured as a double zipper. Such double zippers are known from sports bags or suitcases, for example, the zipper being closed by moving the two zippers towards each other. The zipper is closes completely, if both zippers are in contact with each other. In this state, i.e. when the two zippers are in contact, they can be connected by means of a locking element formed on one or both zippers. Such locking elements are used, for example, in the form of padlocks for suitcases that can also have such double zippers. The double zipper can only be opened, if the locking element is unlocked. The locking element mentioned can further be used to obtain information about whether the support device is currently worn. Thus, if the locking element is locked by a patient, the support device has information about the fact that the support device is currently placed on the body of a patient. In this embodiment, it has to be ensured that the locking element cannot be actuated inadvertently.

In another preferred embodiment of the support device, the closure device can be redundant. This means that a plurality, in particular different kinds of locking elements are provided by which the support device is secured on the body of a patient. For example, a Velcro fastener can be provided that is placed over a zipper.

In particular with a Velcro fastener as the closure device, it can be assumed that the support device has been opened unintentionally, if opening the Velcro fastener has taken a long time. In this case, it is assumed that the Velcro fastener has been "rubbed open" due to an unintentional exertion of force and the support device has been put off or shifted unintentionally. In this case, an alarm can be emitted.

It is further possible to integrate detection devices for detecting the closed state of the closure devices into the closure devices themselves. For example, the hooks of a closure can be configured as switches by which the closed state of the closure can be detected.

The support device 10 illustrated in FIG. 1 is embodied as a waistcoat and can be secured on the body of a patient by means of a zipper 18, for example. In the chest area, the waistcoat 10 has a transmission coil 12 which, for example, can be woven into the fibers of the waistcoat 10. An electric wire 20, which is also integrated in the waistcoat, connects the transmission coil 12 to a voltage source 22 provided on the waistcoat 10.

Along the zipper 18, the waistcoat 10 has five detection devices 26a to 26e, by which the temporal course of the opening of the zipper 18 can be detected.

Further, the waistcoat 10 comprises an input device 28 which can be a key, for example. Using this key, a patient can inform the support device 10 that he has or will put off the same intentionally.

Moreover, the waistcoat has an alarm device, for example a speaker 30, by which an alarm signal can be emitted, if the waistcoat 10 has been put off unintentionally.

Figure 2:
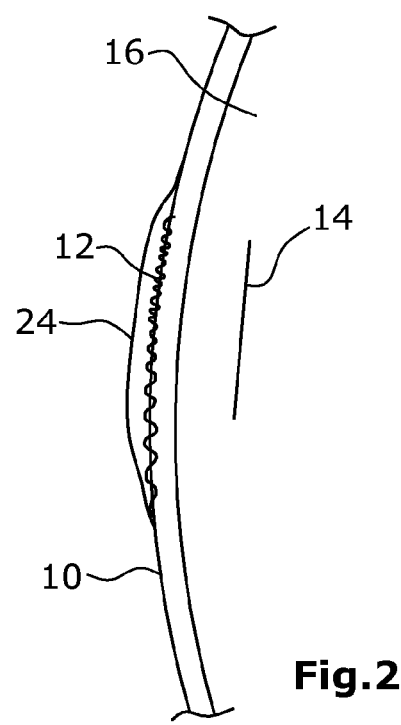
FIG. 2 is a schematic side elevational view of the support device of the present disclosure shown in section.

FIG. 2 is a detail showing a transmission coil 12 woven into the waistcoat 10. In the chest area, the support device 10 has woven-in electrically conductive elements in the form of flexible strands wound in a coil shape and thus forming the transmission coil 12. A concentration of the magnetic field can be achieved by a ferromagnetic foil 24 that covers all of the transmission coil 12 and is arranged on the side of the transmission coil 12 averted from the receiving coil 14. The patient's body is identified by the reference numeral 16.

What is claimed is:

1. A support device for supporting a transmission coil on the body of a patient comprising,
    a receiving or securing device or a receiving space for receiving or securing the transmission coil in and/or on the support device,
    a detection device for detecting a process of putting on the support device, a state of wearing, a process of removal and/or a state of removal of the support device relative to the body of the patient,
    an input device for input of information about an intentional shedding of the support device by the patient into the support device, and
    an alarm device or a connection to an alarm device by a data link, wherein the alarm device is configured to emit an alarm signal if the user has not input information at the input device indicating an intentional shedding of the support device and the alarm device is further configured to emit no alarm signal if the user has input information at the input device indicating an intentional shedding of the support device.

2. The support device of claim 1, further comprising at least one closure device for releasably securing the support device to the body of the patient, wherein the detection device is configured to be located in or in proximity to the at least one closure device such that the detection device can detect an opening of the closure device and, in case of a plurality of closure devices, can detect in particular a temporal course of an opening of the plurality of closure devices.

3. The support device of claim 1, wherein said input device comprises a voice input device or a key.

4. The support device of claim 1, further comprising an offset detection device for detecting an axial and/or radial offset between the transmission coil in or on the support device and a receiving coil adapted to be implanted in the body of the patient,
    wherein in case of an offset exceeding a defined threshold value, the alarm device emits an alarm signal if the patient has not input information at the input device indicating an intentional shedding of the support device.

5. The support device of claim 1, the support device further comprising at least one of:
    an acceleration sensor arranged in a closure device of the support device and/or in the support device itself,
    a sleep detection sensor for detecting a sleeping state of the patient,
    a proximity sensor, and
    a breathing sensor for detecting breathing of the patient.

6. A method for detecting a wearing state of a support device for supporting a transmission coil on the body of a patient, the method comprising the following steps:
    detecting, with a detection device, an action, a chronological sequence of actions and/or a plurality of simultaneous actions of the patient that result in a shedding of the support device or a shifting of the support device relative to the body of the patient,
    evaluating, with the detection device, the detected action, chronological sequence of actions and/or plurality of simultaneous actions of the patient and, subsequently, deciding with the detection device whether the patient has shed and/or shifted the support device intentionally or unintentionally, wherein an intentional shedding and/or shifting of the support device is indicated by the detection device when the patient has input information at an input device indicating an intentional shedding of the support device and an unintentional shedding and/or shifting of the support device is indicated by the detection device when the patient has not input information at an input device indicating an intentional shedding of the support device, and
    emitting an alarm signal with an alarm device when an unintentional shedding and/or shifting of the support device is indicated by the detection device.

7. The method of claim 6, wherein evaluating with the detection device comprises:
    detecting a combination of a plurality of simultaneous or successive actions of the patient with a plurality of sensors in order to indicate whether the shedding or shifting of the support device was intentional or unintentional.

8. The method of claim 6, wherein evaluating further comprises:
    detecting, with at least one sensor, a temporal course of an opening process of at least one closure device by which the support device can be releasably fastened on the body of the patient, wherein an intentional shedding of the support device is indicated if a detected progress of the opening process corresponds to a predefined reference progress within defined threshold values, and otherwise, an unintentional shedding or shifting of the support device is indicated, if the detected progress of the opening process does not correspond to a predefined reference progress within defined threshold values.

\* \* \* \* \*